United States Patent
Okumura et al.

(10) Patent No.: US 8,399,424 B2
(45) Date of Patent: Mar. 19, 2013

(54) METHOD FOR CONTROLLING THE AMOUNT OF GENE PRODUCT, AND AGENT FOR CONTROLLING THE AMOUNT OF GENE PRODUCT

(75) Inventors: Tadayoshi Okumura, Hirakata (JP); Mikio Nishizawa, Ibaraki (JP); Yasuo Kamiyama, Takatsuki (JP); Koji Wakame, Sapporo (JP); Takehito Miura, Sapporo (JP)

(73) Assignees: Amino Up Chemical Co., Ltd, Hokkiado (JP); Kansai Medical University, Osaka (JP)

( * ) Notice: Subject to any disclaimer, the term of this patent is extended or adjusted under 35 U.S.C. 154(b) by 270 days.

(21) Appl. No.: 12/303,908

(22) PCT Filed: Jun. 7, 2007

(86) PCT No.: PCT/JP2007/061564
§ 371 (c)(1),
(2), (4) Date: Dec. 8, 2008

(87) PCT Pub. No.: WO2007/142303
PCT Pub. Date: Dec. 13, 2007

(65) Prior Publication Data
US 2010/0227318 A1 Sep. 9, 2010

(30) Foreign Application Priority Data
Jun. 8, 2006 (JP) .................................. 2006-159729

(51) Int. Cl.
*A61K 31/70* (2006.01)
*C07H 21/02* (2006.01)
*C07H 21/04* (2006.01)
*C12Q 1/68* (2006.01)

(52) U.S. Cl. .................. 514/44 A; 514/44 R; 536/23.1; 536/24.1; 536/24.5

(58) Field of Classification Search ........................ None
See application file for complete search history.

(56) References Cited

U.S. PATENT DOCUMENTS

| 2007/0042979 A1 | 2/2007 | Yano et al. | |
|---|---|---|---|
| 2008/0020990 A1 | 1/2008 | Yano et al. | |
| 2010/0248364 A1* | 9/2010 | Okumura et al. | 435/375 |

FOREIGN PATENT DOCUMENTS

| JP | 2005-013224 A | 1/2005 |
|---|---|---|
| JP | 2005-524393 A | 8/2005 |
| WO | 03/070744 A1 | 8/2003 |
| WO | 2004/105774 A1 | 12/2004 |
| WO | 2004/106511 A1 | 12/2004 |

OTHER PUBLICATIONS

Matsui et al., Hepatology vol. 47(2):686-697, 2008.*
Hemmrich et al., Nitric Oxide vol. 12:183-199, 2005.*
Jacquelyn J. Maher et al.; "Adenovirus-Mediated Expression of Cytokine-Induced Neutrophil Chemoattractant in Rat Liver Induces a Neutrophilic Hepatitis;" Hepatology; vol. 25; No. 3; 1997; pp. 624-630.
Riitta Keinanen et al.; "Molecular Cloning and Characterization of the Rat Inducible Nitric Oxide Synthase (iNOS) Gene;" Gene 234; 1999; pp. 297-305.
Qianhong Li et al.; "Gene Therapy With Inducible Nitric Oxide Synthase Protects Against Myocardial Infarction via a Cyclooxygenase-2-Dependent Mechanism;" Circulation Research; 2003; pp. 741-748.
Jiu-Haw Yin et al.; "Inducible Nitric Oxide Synthase Neutralizes Carbamoylating Potential of 1,3-Bis(2-chloroethyl)-1-nitrosourea in C6 Glioma Cells;" The Journal of Pharmacology and Experimental Therapeutics; vol. 297; No. 1; 2001; pp. 308-315.
Yoshiki Nishimura et al.; "Antisense Transcript and RNA Processing Alterations Suppress Instability of Polyadenylated mRNA in Chlamydomonas Chloroplasts;" The Plant Cell; vol. 16; Nov. 2004; pp. 2849-2869.
Satoko Yoshizawa et al.; "Nuclease Resistance of an Extraordinarily Thermostable Mini-hairpin DNA Fragment, d (GCGAAGC) and Its Application to In Vitro Protein Synthesis;" Nucleic Acids Research; vol. 22; No. 12; 1994; pp. 2217-2221.
S. Katayama et al.; "Antisense Transcription in the Mammalian Transcriptome;" Science; vol. 309; Sep. 2, 2005; pp. 1564-1566.
Tala Bakheet et al.; "ARED 2.0: An Update of AU-rich Element mRNA Database;" Nucleic Acids Research; vol. 31; No. 1; 2003; pp. 421-423.
Masanori Yamada et al.; "Characterization of Alternatively Spliced Isoforms of the Type I Interleukin-1 Receptor on iNOS Induction in Rat Hepatocytes;" Nitric Oxide 17; 2007; pp. 98-105.
Robb, G Brett et al.; "Post-transcriptional regulation of endothelial nitric-oxide synthase by an overlapping antisense mRNA transcript"; Journal of Biological Chemistry, vol. 279, No. 36, Sep. 3, 2004, pp. 37982-37996.
Alderton, Wendy K et al.; "Nitric oxide synthases: Structure, function and inhibition"; Biochemical Journal, vol. 357, No. 3, Aug. 1, 2001, pp. 593-615.
Korneev, Sergei A. et al.; Novel noncoding antisense RNA transcribed from human anti-NOS2A locus is differentially regulated during neuronal differentiation of embryonic stem cells. RNA (Cold Spring Harbor), vol. 14, No. 10, Oct. 2008, pp. 2030-2037.
Lavorgna et al. "In search of antisense", Trends in Biochem Sciences, vol. 29, No. 2, Feb. 2004, pp. 88-94.

* cited by examiner

*Primary Examiner* — Sean McGarry
(74) *Attorney, Agent, or Firm* — Sughrue Mion, PLLC

(57) ABSTRACT

The invention relates to a method of intracellularly controlling amounts of gene products, which can increase an amount of gene product intracellularly, comprising a step of introducing into the cell a substance having a sequence complementary to the base sequence of mRNA corresponding to the gene product, its precursor or another substance which can have equivalent action in the cell.

3 Claims, 6 Drawing Sheets

METHOD FOR CONTROLLING THE AMOUNT OF GENE PRODUCT, AND AGENT FOR CONTROLLING THE AMOUNT OF GENE PRODUCT

TECHNICAL FIELD

The present invention relates to a method for intracellularly controlling amounts of gene products, particularly relates to a method for increasing the production amount and a production-controlling agent.

BACKGROUND ART

Conventionally, a method called RNAi (RNA interference), where transcription is repressed by cutting target mRNA in a double-stranded RNA, has been known. Usually, RNAi involves base length of about 20 base pairs and a screening method for its double-stranded oligonucleotide and antisense RNA has been disclosed (Patent Document 1: Japanese Patent Application Laid-Open No. 2005-13224).

Also, compounds useful in controlling interleukin genes, interleukin superfamily genes, expression of genes and/or expression and activities of genes involved in interleukin routes of activities, by RNA interference (RNAi) using small nucleic acid molecules such as short interfering nucleic acid (siNA), short interfering RNA (siRNA), double-stranded RNA (dsRNA), microRNA (miRNA), and short hairpin RNA (shRNA) molecules have been disclosed (Patent Document 2:Japanese Patent Application Laid-Open No. 2005-524393).

If antisense RNA exists in a cell, gene expression can be inhibited by hybridizing with complementary mRNA to inhibit translation from mRNA to proteins. If antisense RNA is artificially introduced into a cell, expression of target gene can be inhibited. Therefore, this technique is currently used as a technique shedding light on gene functions and its application into medicinal products has been studied. However, there are many unknown points in what mode RNA exists in a cell and therefore there are many points unclear as to controlling of its expression with transcription process from mRNA to protein as target.

[Patent Document 1] Japanese Patent Application Laid-Open No. 2005-13224
[Patent Document 2] Japanese Patent Application Laid-Open No. 2005-524393

DISCLOSURE OF INVENTION

[Problem to be Solved by Invention]
The present invention provides a method for intracellularly controlling the amount of gene products, particularly provides a method for increasing the amount and a production-controlling agent.

[Means for Solving the Problem]
The present inventors have found out that there are some cases where a single-stranded RNA (antisense transcript: usually considered as a transcript of an antisense chain of DNA, but the origin is no object here) having a complementary sequence to mRNA is present in a cell, which is different from conventional antisense RNA and contributes to stabilization of mRNA. Based on this finding, they have completed the present invention.

That is, the present invention relates to a method for controlling an amount of gene product, a method for screening the gene products to which the said controlling method can be applied and an agent controlling an amount of gene product.

1. A method for increasing an amount of gene product intracellularly, comprising a step of introducing into the cell a substance having a sequence complementary to the base sequence of mRNA corresponding to the gene product, its precursor or another substance which can have equivalent action in the cell.
2. The method for increasing an amount of gene product according to 1, wherein the substance having a sequence complementary to the base sequence of mRNA corresponding to the gene product, its precursor or another substance which can have equivalent action in the cell is a substance which contributes to stabilization of mRNA in the cell.
3. The method for increasing an amount of gene product according to 1 or 2, wherein the gene product is cytokine or its precursor.
4. The method for increasing an amount of gene product according to any one of 1 to 3, wherein the gene product is inducible nitric oxide synthase (iNOS).
5. A method for screening gene products in which the method for increasing an amount of gene product according to 1 can be applied, comprising a step of determining presence or absence of an antisense transcript containing a sequence complementary to the base sequence of mRNA corresponding to the gene product.
6. The method for screening gene products according to 5, wherein the determination step of antisense transcript is carried out by conducting reverse transcription from intracellular mRNA by using a primer containing sense sequence of 5' end and 3' end of mRNA corresponding to the gene product or a part of sense sequence in the vicinity of these ends and thereby confirming presence or absence of product of the reverse transcription.
7. The method for screening gene products according to 5 or 6, further comprising a step of introducing into the cell an oligonucleotide which can be hybridized to a base sequence contained in the antisense transcript or its derivative and then observing increase and decrease in the amount of the gene product.
8. A substance, containing a sequence complimentary to all or part of cytokine mRNA sequences, which increases the synthesis amount of the cytokine.
9. An agent for controlling a production amount of cytokine, comprising the substance according to 8.
10. A substance, containing a sequence complimentary to all or part of inducible nitric oxide synthase (iNOS) mRNA, which increases the synthesis amount of inducible nitric oxide synthase (iNOS).
11. A substance, containing Sequence No. 1 or a base sequence with homology of 75% or more to Sequence No. 1, which increases the synthesis amount of inducible nitric oxide synthase (iNOS).
12. A RNA, containing a base sequence corresponding to a sequence obtained from cDNA derived from intracellular mRNA through reverse transcription by using a primer containing sense sequence of 5' end and 3' end of inducible nitric oxide synthase (iNOS) mRNA corresponding to the gene product or a part of sense sequence in the vicinity of these ends, which increases the synthesis amount of inducible nitric oxide synthase (iNOS).
13. An agent for controlling expression of iNOS mRNA, comprising the substance according to any one of 10 to 12.

[Effect Of Invention]
According to the present invention, by using a substance having a sequence complementary to the base sequence of gene mRNA corresponding to a gene product, its precursor or another substance which can have equivalent action in the cell, generation of the gene product can be suppressed. This technique can be applied in a wide range of fields, for example, it is useful in treatment and prevention of diseases including cancers, auto immune diseases and inflammatory disease.

BEST MODE FOR CARRYING OUT THE INVENTION

In the present invention, by using a substance having a sequence complementary to the base sequence of gene mRNA corresponding to a specific gene product, its precursor or another substance which can have equivalent action in the cell, the amount of the gene product can be increased.

That is, in a conventional method of controlling expression amount by using antisense RNA, it is assumed that the method involves a process where hybridization of antisense RNA with sense RNA suppresses translation while in the present invention, a substance which is the same as or similar to antisense transcript increases the amount of the gene product of sense chain. Although details of its mechanism are unknown, it is assumed, for example, that antisense transcript contributes to stabilization of sense mRNA in the cell, which clearly distinguishes the present invention in the action mechanism from conventional methods of controlling expression amount using antisense RNA. Generally, the substance having a sequence complementary to the base sequence of mRNA corresponding to a specific gene product, its precursor or another substance which can have equivalent action in the cell, needs to have a base length of 30% or more, preferably 50% or more, more preferably 70% or more, based on the base sequence of the mRNA. Typically, it is a RNA chain and may be partly modified or it may be linked with other substances (such as proteins, sugars and low molecular substance). Any precursor may be used as long as it is converted into the above-described substance in the cell into which it is introduced or in the living body to which the agent is administered through metabolism.

In order to determine effectiveness of the method of the present invention on a gene product, it is first checked whether or not antisense transcript containing a sequence complementary to the base sequence of mRNA corresponding to the gene product is present in the cell. The determination on presence of the antisense transcript is made by conducting reverse transcription using a primer containing a part of sense sequence of 5' and 3' ends of mRNA corresponding to the gene product or in the vicinity of these ends and checking presence or absence of reverse transcription product (cDNA). After synthesis of cDNA, the cDNA is amplified by PCR method and the whole structure may be determined, for example, by RACE method.

In a case where presence of antisense transcript has been confirmed, a substance having a sequence complementary to the base sequence of a mRNA, its precursor or another substance which can have equivalent action in the cell (hereinafter, referred to as "Invention Substance") or an oligonucleotide or its derivative which can be hybridized to a base sequence contained in antisense transcript (hereinafter, referred to as "sense oligo") is introduced into the cell and increase and decrease in the amount of the gene product are observed. If administration of Invention Substance increases the expression amount of the gene product (the original gene product), positive control is possible in contrast to conventional antisense RNA. Further, it is assumed that sense oligo, when reacted with (hybridized to) antisense transcript, reduces the effective amount of antisense transcript in the cell and therefore, if administration of sense oligo reduces the expression amount of the gene products (the original gene product), it can be assumed that antisense transcript participates in positively controlling the expression amount.

In the present Description, when "positive control of expression amount" is mentioned, it includes not only cases increase in expression amount by antisense transcript but also maintaining the expression amount in a case where the expression amount would be decreased without administration of antisense transcript.

As described above, as long as (1) antisense transcript for the objective gene products exists in the cell and (2) the antisense transcript contributes to controlling (especially in positive control) the expression amount of the gene product (the original gene product), the method of the present invention is effective. Accordingly, gene products to which the present invention can be applied can be easily screened by the above methods (1) and (2). Recently, presence of quite many kinds of such antisense transcripts has been discovered (see Science 309: 1564-1566 (2005)). Examples of Invention Substance include various kinds. For example, the present invention is especially useful when the gene products are cytokines, cyclooxygenase-2 (COX-2), CINC-1 (cytokine-induced neutrophil chemoattractant 1), NF-κB p50, IκB-α or chemokines which are closely related with inflammation, or inducible nitric oxide synthase (iNOS) or its precursor. There is no limitation on species from which the gene product derives.

The antisense transcript comprising a base sequence complementary to an inducible nitric oxide synthase (iNOS) mRNA contains a base sequence corresponding to a sequence obtained from complementary DNA (cDNA) through reverse transcription using a sense-chain primer of the iNOS mRNA (including a primer hybridizing only to mRNA (a primer specific to strand (chain)).

The Invention Substance comprising a base sequence complementary to mRNA of iNOS is a nucleotide containing a base sequence identical to or substantially identical to a base sequence represented by Sequence No.1. The nucleotide having a "substantially" identical sequence is a substance containing Sequence No.1 or containing a sequence having homology of 75% or more, preferably 90% or more, more preferably 95% or more with Sequence No.1, which increases synthesis amount of inducible nitric oxide synthase (iNOS).

Invention Substance as a substance having a sequence complementary to the base sequence of mRNA, its precursor or another substance which can have equivalent action in the cell can be prepared by methods of chemical synthesis, known expression methods and known purification methods or the method described in Examples.

Further, the present invention encompasses agents for controlling the production amount of cytokine, especially for controlling the production amount of iNOS, which contain these antisense transcripts.

The above-described sense oligonucleotide (sense oligo) having a sequence complementary to a antisense transcript of iNOS mRNA is an oligonucleotide hybridizable to the antisense transcript or a derivative thereof. The sense oligo has only to be modified not to be decomposed by nucleolytic enzyme in the nucleus.

Designing of sense oligo can be made with a program "mfold" disclosed in Nucleic Acids Res. 31, 3406-3415 (2003) and in J. Mol. Biol. 288, 911-940 (1999) (see http://www.bioinfo.rpi.edu/~zukerm/rna/) by predicting a secondary structure of RNA. As candidate sequence for the sense oligo, a sense oligonucleotide is designed for portions thermodynamically unstable (for example, non-stem region in a stem-loop structure), preferably a portion including a loop in the stem-loop structure.

With respect to the above candidate sequence of the sense oligo, a sequence not including a sequence which causes sequence-nonspecific reaction in a cell, such as 5'-CG-3'5'-GGGG-3' or 5'-GGGGG-3' is selected. Further, after confirming that no analogous sequence exists by conducting homology search in the rat genome, a preferred sequence is selected (see J. Neurochem. 86, 374-382 (2003)).

Examples of sense oligo include the following oligonucleotides.

(Modifications of the Following Sequences are Omitted Here.)

```
5'-GCCTCATACTTCCTCAGAGC-3'    (Sequence No. 36)

5'-TAGCTGCATTGTGTACAGAT-3'    (Sequence No. 37)

5'-GTGTATAATTCCTTGATGAA-3'    (Sequence No. 38)
```

These can be prepared by chemical synthesis, known expression or purification methods, or methods described in Examples.

There is no particular limitation on modifications of sense oligo as long as the sense oligo is modified not to be decomposed by nucleolytic enzyme present in the nucleus. In a cell, a sense oligonucleotide is digested from both ends by an enzyme, exonuclease, which removes nucleotides sequentially from the 5' end and 3' end. For example, it is preferable that the sense oligo be modified to be a phosphorothioate type stable to degrading enzymes, in which one or more phosphate bonds P=O from both ends are substituted with P=S. (Hereinafter, this is referred to as "phosphorothioate sense oligonucleotide (phosphorothioate sense oligo).") (See J. Neurochem. 86, 374-382 (2003).) However, if all phosphate bonds are modified into phosphorothioate, optical isomers are generated, which is disadvantageous in light of hybridization.

Examples of phosphorothioate sense oligonucleotide (phosphorothioate sense oligo) include

```
5'-G*C*C*TCATACTTCCTCAG*A*G*C-3',
and

5'-T*A*G*CTGCATTGTGTACA*G*A*T-3'
and

5'-G*T*G*TATAATTCCTGAT*G*A*A-3'.
```

(In the sequences, * shows a portion modified into phosphorothioate.)

Examples of other modifications include PNA (peptide nucleic acids), LNA (Locked Nucleic Acids), ENA (2'-O, 4'-C-Ethylene-bridged Nucleic Acids; product of Sigma-Aldrich Corporation), Morpholino) and Oligo (product of Gene Tools LLC, OR, USA).

It is assumed that, by introducing a sense oligo into a cell in which presence of antisense transcript of iNOS mRNA has been confirmed, the sense oligo reacts with the antisense transcript (hybridization) to thereby reduce the effective amount of the antisense transcripts in the cell. Therefore, by administering a sense oligo, the original expression amount of a gene product (iNOS) can be decreased to thereby suppress excessive production of NO.

EXAMPLES

The present invention is specifically described by way of Examples hereinbelow. The present invention is not limited to these Examples.

(1) Method for Determining a Sequence and Region (Base Length) of an Antisense Transcript Complementary to a Sequence of iNOS mRNA Example 1

Antisense Transcript of Rat iNOS

Examination was made on mRNAs of rat iNOS by the following method, as to whether or not "antisense transcript" transcribed from gene antisense chain was present. Studies were made on what role this "antisense transcript" played in controlling generation of gene products. The base sequences of the rat iNOS mRNAs are known as shown in DDBJ/EMBL/GenBank International Nucleotide Sequence Database (http://www.ddbj.nig.ac.jp/,http://www.ebi.ac.uk/embl/,ht tp://www.ncbi.nlm.nih.gov/Genbank/).

In the 3'-untranslated region (3'UTR) of mRNA of a gene causing inductive expression, such as cytokine and acute phase proteins, a sequence called AU-rich element (ARE), that is, a sequence of 5'-AUUUA-3' or 5'-AUUUUA-3' is present (see Proc Natl Acad Sci USA 83: 1670-1674 (1986)). Since ARE is also present in 3' UTR of human, rat and mouse iNOS mRNAs, examination was made on whether or not an antisense transcript corresponding to 3'UTR containing the ARE (and having a complementary sequence) was present by chain-specific RT-PCR method. The method is a method of measuring an amount of mRNA after synthesizing complementary DNA (cDNA) through reverse transcription using a strand (chain)-specific primer such as oligo dT primer hybridizing only to mRNA and then amplifying cDNA by PCR method.

That is, by using the following primer of iNOS gene sense chain: 5'-TGCCCCTCCCCCACATTCTCT-3'(Sequence No.2), RT-PCR was conducted on all the RNA of rat primary-cultured hepatocyte in which iNOS mRNAs were induced by adding IL-1β to the culture medium, to thereby synthesize cDNAs.

After mixing RNAs (1 μg) prepared from rat primary-cultured hepatocytes with 2 pmol primer, the mixture was heated at 70° C. for 10 minutes and then rapidly cooled to 0° C. To this, ReverTra Ace reaction buffer (manufactured by TOYOBO CO., LTD.), dNTP(N=A,C,G,T) (so that the final concentration is 1 mM), 20 units RNase inhibitor (manufactured by TOYOBO CO., LTD.) and 200 units of ReverTra Ace reverse transcription enzyme (manufactured by TOYOBO CO., LTD.) were added to thereby make the total amount 25 μl. The mixture was retained at 47° C. for 60 minutes to allow reverse transcription to proceed. Then, the mixture was heated at 70° C. for 15 minutes to thereby deactivate the reverse transcription enzymes. Next, 5 units of Tth RNase H (manufactured by TOYOBO CO., LTD.) were added and the mixture was heated at 37° C. for 20 minutes, to thereby decompose template RNAs. The synthesized cDNAs were collected through ethanol precipitation and dissolved in 20 μl of TE buffer.

To 2 μl of thus obtained cDNAs, PCR reaction buffer (manufactured by NIPPON GENE CO., LTD.), dNTP(N=A, C,G,T; manufactured by NIPPON GENE CO., LTD.) (so that the final concentration is 125 μM), the following two kinds of primers, forward primer 40 pmol and Reverse primer 40 pmol, 1 unit of Gene Taq DNA polymerase (manufactured by NIPPON GENE CO., LTD.) and anti-Taq high(=anti-Taq polymerase antibody, manufactured by TOYOBO CO., LTD.) were added, to thereby make the total amount 40 μl and further, PCR was conducted.

```
Forward direction:
5'-ACCAGGAGGCGCCATCCCGCTGC-3'    (Sequence No. 3)

Reverse direction:
5'-CTTGATCAAACACTCATTTTATTAAA-3' (Sequence No. 4)
```

The temperature protocol for PCR was carried out according to a known method, that is, step-down method (see Nishizawa M, Nakajima T, Yasuda K, Kanzaki H, Sasaguri Y, Watanabe K, and Ito S. Close kinship of human 20a-hydroxysteroid dehydrogenase gene with three aldo-keto reductase genes. Genes Cells (2000) 5, 111-125). Detection of the PCR product was performed by agarose gel electrophoresis and as a result, amplification of the band of 186 base pairs (bp) was observed.

This band was cut out of the gel and purified, and the base sequence was determined. It was confirmed that the sequence was a sequence of 3'UTR of rat iNOS mRNA sandwiched between the above primer sequences. That is, presence of antisense transcript was evidenced by chain-specific RT-PCR method using a sense primer of iNOS gene.

Further, in order to elucidate the whole structure of antisense transcript of iNOS gene, analysis attempts were made according to RACE method (see Frohman M A. Rapid amplification of complementary DNA ends for generation of full-length complementary DNAs: thermal RACE. Methods Enzymol. (1993) 218: 340-356). RACE method is a method of conducting reverse transcription by preparing a chain-specific primer from a known cDNA sequence and determining the sequences of 5' and 3' ends of the cDNA.

[Determination of 5'-Side Sequences of cDNA]

IL-1β was added to rat primary-cultured hepatocytes to thereby induce iNOS mRNAs and by using Trizol reagent (manufactured by Invitrogen Corporation), RNAs were prepared. By using the RNAs as templates and a primer of Sequence No.2 (sense (forward) primer of iNOS; 5'-TGC-CCCTCCCCCACATTCTCT-3'), double-stranded cDNAs were synthesized. To the cDNAs, a CA cassette adapter (attachment to cDNA PCR Library Kit manufactured by TAKARA BIO INC.) was connected and then by using a primer of Sequence No. 3 (sense (forward) primer for 3'UTR of iNOS mRNA) and CA primer (attachment to cDNA PCR Library Kit manufactured by TAKARA BIO INC.), PCR was conducted. The reaction solution was subjected to agarose gel electrophoresis and as a result, amplification of a band of about 250 bp size was observed. This band was cut out and subjected to cloning into pGEM-T Easy vector (manufactured by Promega Corporation), to thereby determine the base sequence.

[Determination of 3'-Side Sequences of cDNA]

From rat primary-cultured hepatocytes induced by IL-1β, RNAs were prepared in the same manner as described above. By using PolyATract mRNA Isolation System (manufactured by Promega Corporation), RNAs of PolyA⁻ fraction was refined and by using the RNAs as templates and a random primer having an anchor sequence (underlined) thereto (anchor random primer; 5'-TTCCCTCCCGTTTTCTCTGCC ACTAGAATTCTCGAGCGGCCGCNNNNNNNN-3' (Sequence No.5), double-stranded cDNAs were synthesized. To this cDNA, a CA cassette adapter was connected and then by using a primer of Sequence No.4 (antisense (reverse) primer for 3'-UTR of iNOS Mrna) and CA primer, PCR was conducted. The reaction solution was purified and used as template to perform a secondary PCR by using an antisense (reverse) primer for 3'-UTR of iNOS mRNA (5'-ATATTA-GAGCAGCGGGATGGCGCCTC-3'(Sequence No. 6)) and an anchor primer (5'-ACTAGAATTCTCGAGCGGCCGC-3' (Sequence No.7): a primer for the anchor sequence of the above "anchor random primer"). The reaction solution was subjected to agarose gel electrophoresis and as a result, amplification of a band of about 200 to 500 by size was observed. This band was cut out and subjected to cloning into pGEM-T Easy vector, to thereby determine the base sequence.

As a result, the total length of the antisense transcript was estimated to be about 600 bases or more. The sequence is shown below. (sequence No.1; shown as cDNA sequence) That is, the antisense transcript corresponded to 3'-UTR of iNOS mRNA and its transcriptional start site (5' side) was on the complementary chain of a polyA-added site in the iNOS mRNA.

Example 2

Antisense Transcript of Human iNOS

By the following method, it was checked in a human iNOS mRNA whether or not "antisense transcript" transcribed from an antisense chain of a gene exists. The base sequences of human iNOS mRNAs have been made public by DDBJ/EMBL/GenBank International Nucleotide Sequence Data Base (http://www.ddbj.nig.ac.jp/, http://www.ebi.ac.uk/embl/ and http://www.ncbi.nlm.nih.gov/Genbank/).

All RNAs were extracted from a human tissue (placenta, liver and gastric mucous membrane) or human cells (lymph cell not stimulated) according to a conventional method by using Trizol reagent (product of Invitrogen Corporation). The obtained all the RNAs were treated with TURBO DNA-free Kit (product of Applied Biosystems.) including DNase to thereby remove genomic DNAs mixed therein. With all the RNAs as templates, reverse transcription was conducted by using the following primer of a sense chain of human iNOS gene: 5'-CTGAGTGCACCACTTCAAGTGAC-3' (Sequence No.8), to thereby synthesize cDNA. Specifically, cDNA was synthesized in the same manner as in Example 1 except that in place of 1 μg of RNA prepared from rat primary-cultured hepatocyte and 2 pmol of primer represented by Sequence No.2, all RNAs (1 μg) prepared from a human tissue or cell and the primer (2 pmol) represented by the above sequence No.8 were used.

To 2 μl of thus obtained cDNAs, PCR reaction buffer (manufactured by NIPPON GENE CO., LTD.), dNTP(N=A, C,G,T; manufactured by NIPPON GENE CO., LTD.) (so that the final concentration could be 125 μM), the following two kinds of primers, forward primer 40 pmol and Reverse primer 40 pmol, 1 unit of Gene Taq DNA polymerase (manufactured by NIPPON GENE CO., LTD.) and anti-Taq high(=anti-Taq polymerase antibody, manufactured by TOYOBO CO., LTD.)# were added, to thereby make the total amount 40 μl and further, PCR was conducted.

```
Forward direction:
5'-CAGGAGGTGCTATCGCACCACT-3'     (Sequence No. 9)

Reverse direction:
5'-GCAATTCATGTAAATATCTCCATC-3'   (Sequence No. 10)
```

The PCR was carried out in the same manner as in Example 1. Detection of the PCR product was performed by agarose gel electrophoresis and as a result, amplification of the band of 151 base pairs (bp) was observed in the case using cDNAs derived from human placenta. No amplification was observed in cases using other cDNAs (derived from liver, gastric mucous membrane and lymph cell not stimulated).

This amplified band was cut out of the gel and purified, and the base sequence was determined. It was confirmed that the sequence was a sequence complementary to of 3'UTR of human iNOS mRNA sandwiched between the above primer sequences. That is, presence of antisense transcript of human iNOS was evidenced by chain-specific RT-PCR method using a sense primer of iNOS gene. The sequence of human iNOS antisense transcript is shown as Sequence No. 11, in terms of cDNA sequence.

Example 3

Antisense Transcript of Mouse iNOS

By the following method, it was checked in a mouse iNOS mRNA whether or not "antisense transcript" transcribed from an antisense chain of a gene exists. The base sequence of mouse iNOS mRNA has been made public by DDBJ/EMBL/GenBank International Nucleotide Sequence Database (http://www.ddbj.nig.ac.jp/, http://www.ebi.ac.uk/embl/ and http://www.ncbi.nlm.nih.gov/Genbank/).

All RNAs were extracted from a RAW 264 cell according to a conventional method by using Trizol reagent (product of Invitrogen Corporation). All the obtained RNAs were treated with TURBO DNA-free Kit (product of Applied Biosystems.) including DNase to thereby remove genomic DNAs mixed therein. With all the RNAs as templates, reverse transcription was conducted by using the following primer of a sense chain of mouse iNOS gene: 5'-CCTTCTTCTC-CACTCCCCAGCT-3'(Sequence No. 12), to thereby synthesize cDNAs. Specifically, cDNAs were synthesized in the same manner as in Example 1 except that in place of 1 μg of RNAs prepared from rat primary-cultured hepatocytes and 2 pmol of primer represented by Sequence No.2, all RNAs (1 μg) prepared from RAW 264 cells and the primer (2 pmol) represented by the above sequence No.12 were used.

To 2 μl of thus obtained cDNAs, PCR reaction buffer (manufactured by NIPPON GENE CO., LTD.), dNTP(N=A, C,G,T; manufactured by NIPPON GENE CO., LTD.) (so that the final concentration could be 125 μM), the following two kinds of primers, forward primer 40 pmol and reverse primer 40 pmol, 1 unit of Gene Taq DNA polymerase (manufactured by NIPPON GENE CO., LTD.) and anti-Taq high(=anti-Taq polymerase antibody manufactured by TOYOBO CO., LTD.)# were added, to thereby make the total amount 40 μl and further, PCR was conducted.

```
Forward direction:
5'-GACCACCAGGAGGCACCATGCCG-3'    (Sequence No. 13)

Reverse direction:
5'-ATACAGGAAAGGCCCAAGCCATC-3'    (Sequence No. 14)
```

The PCR was carried out in the same manner as in Example 1. Detection of the PCR product was performed by agarose gel electrophoresis and as a result, amplification of the band of 127 base pairs (bp) was observed.

This amplified band was cut out of the gel and purified, and the base sequence was determined. It was confirmed that the sequence was a sequence complementary to 3'UTR of mouse iNOS mRNA sandwiched between the above primer sequences. That is, presence of antisense transcript of mouse iNOS was evidenced by chain-specific RT-PCR method using a sense primer of iNOS gene. The sequence of mouse iNOS antisense transcript is shown as Sequence No. 15, in terms of cDNA sequence.

(2) Stabilization of iNOS mRNA by Antisense Transcript Complementary to iNOS mRNA (Hereinafter, Simply Referred to as Antisense)

Example 4

Stabilization of iNOS mRNA by Antisense Transcript of Rat iNOS

In order to clarify whether or not a rat antisense stabilizes iNOS mRNAs, a sense ologonucleotide of iNOS (hereinafter, simply referred to as sense oligo) having a sequence complementary to the antisense and having a property of hybridizing to the rat antisense) was introduced into rat primary-cultured hepatocyte and the amount of iNOS mRNA was measured. The sense oligo prevented decomposition of oligonucleotide caused by nucleolytic enzymes in the cell by substituting one of oxygen atoms in phosphoric acid in phosphodiester linkage with a sulfur atom (phosphorothioate). By using gene introduction reagent kit (MATra-A Reagent, manufactured by IBA GmbH (Gottingen, Germany)) according to Magnet assisted transfection method, the phosphorothioated sense oligo was introduced to rat primary-cultured hepatocyte.

Rat primary-cultured hepatocytes were prepared according to a known method (J. Hepatol. 40, 616-623, 2004) and sowed in a 6-hole plate ($3\times10^5$ cells per well). After 2 hours, the medium was changed to a new medium of 1.5 ml per well (Williams' E medium (WE) containing 10% fetal bovine serum, 10 nM dexamethasone and 10 nM insulin: hereinafter simply referred to WES-D1). Further after 4 hours, oligo (2 μg) and WE (200 μl) were mixed together. Then, 2 μl of MATra-A Reagent (manufactured by IBA GmbH) was blended therein and the mixture was left standing still at room temperature for 20 minutes. Then, all the amount of the mixture was added dropwise to wells containing hepatocytes. The 6-hole plate was placed on a magnetic disk (manufactured by IBA GmbH) and left standing still at room temperature for 15 minutes, to thereby introduce oligo into the cells. After changing the medium to a WE containing 10'% fetal bovine serum (1.5 ml per well), it was left standing still overnight at 37° C. The next morning, after the medium was changed to a WE medium containing 1 nM IL-1β and left standing at 37° C. for 4 hours, all RNAs were prepared.

When hepatocyte is stimulated with IL-1β, the amount of iNOS mRNA remarkably increases. After the above phosphorothioated sense oligo was introduced to the hepatocyte and the cells were stimulated with IL-1β, the amount of mRNA was measured by RT-PCR method and real-time PCR method. The results are shown in FIGS. 1 and 2.

The sense-chain sequences of iNOS gene used here, that is, phosphorothioated oligonucleotide having the same sequence as that of the iNOS mRNA, are shown by the following sequences. In the experiments, the sequences correspond to S2, S4 and S5 respectively.

```
S2: 5'-G*C*C*TCATACTTCCTCAG*A*G*C-3'

S4: 5'-T*A*G*CTGCATTGTGTACA*G*A*T-3'

S5: 5'-G*T*G*TATAATTCCTTGAT*G*A*A-3'
    (Phosphorothioated sites are shown with "*".)
```

On the other hand, as a negative control, "scramble oligo", which had been confirmed to have the same base composition as the iNOs mRNA but have a different sequence and not to hybridize to iNOS mRNA, its transcript or other RNAs, was introduced. The sequences of the scramble oligos are shown below.

```
Scr2:     5'-G*G*T*ATTGCCCACCCAAC*T*C*T-3'

Scr4:     5'-G*G*C*TCCATATGATTAGA*T*G*T-3'

Scr5:     5'-G*A*T*TGTTACTTAGAGAC*T*A*T-3'
```

These scramble oligos, like sense oligo, were used after phosphorothioated for the purpose of preventing decomposition in the cells. In terms of "scramble oligo", it was confirmed through homology search with rat genome that there were no analogous sequences.

Further, as another negative control, a phosphorothioate sense oligonucleotide S1 for stem portion of stem-loop structure of iNOS mRNA was introduced. The sequence of S1 is shown below. S1:5'-C*A*T*TCTCTTTCCTTTGC*C*T*C-3'
("*" means the same meaning as above described.)

If chain-specific PCR method is performed by using a primer having the same sequence as the sequence of a sense chain (a chain having the same sequence as the sequence of mRNA), only cDNA against "antisense transcript" is reverse-transcribed and therefore, the amount of "antisense transcript" can be measured By preparing a control on which PCR was carried out without reverse transcription, it was confirmed that genomes got mixed in all RNAs of hepatocytes were not amplified by PCR. In the Figure, it was shown as RT(−).

As a result, in a case where phosphorothioated sense oligos of S2, S4 and S5 were introduced, the amount of iNOS mRNAs was decreased. This is because phosphorothioated sense oligo was hybridized to antisense transcript of iNOS to thereby decompose antisense transcripts, showing that iNOS mRNAs were also decomposed. On the other hand, in a case scramble oligo was introduced, there was no significant change in the amount of iNOS mRNA. Also, in a case where S1 corresponding to a stem portion was introduced, there was no significant change in the amount of iNOS mRNA.

In a case where sense oligo S5 or scramble oligo Scr 5 was introduced into a hepatocyte, the amount of iNOS mRNAs after adding IL-1β was measured by real-time PCR with cDNA prepared through reverse transcription being used as templates. As a result, in a case where scramble oligo Scr 5 was introduced, it took 119 minutes to double the amount of iNOS mRNAs while in case of sense oligo S5, it took 461 minutes. (See FIG. 2.)

Like iNOS, CINC1 (cytokine-induced neutrophil chemoattractant 1) causes remarkable induction of mRNA in hepatocyte under stimulation by IL-1β. Moreover, also in mRNA 3'-untranslated region (3'UTR) of CINC1, an ARE sequence exists, like in iNOS mRNA. When iNOS sense oligo was introduced into hepatocyte and the amount of mRNA of CINC1 was measured, there was no difference in the mRNA amount as compared with a case where no sense oligo was introduced. That is, it showed that action of iNOS sense oligo was limited to iNOS (FIG. 1).

Based on all the results, it was shown that the iNOS sense oligo, which hybridized specifically to iNOS antisense transcript to thereby promote decomposition of iNOS mRNA, specifically decreased the iNOS mRNA amount.

Example 5

Stabilization of iNOS mRNA by Antisense Transcript of Mouse iNOS

A phosphorothioate sense oligo of iNOS sense oligonucleotide having a property of being hybridized to mouse antisense was introduced into RAW 264 cells derived from mouse macrophage and observation was made on iNOS-expression suppressing action of mouse antisense transcript.

The procedures not described below were carried out in the same manner as in Example 4. Mouse RAW 264 cells were sown $5\times10^5$ cells per well, DMEM medium was changed and the cells were cultured in a constant-temperature $CO_2$ incubator.

By Magnet assisted transfection method of IBA GmbH (Gottingen, Germany), a phosphorothioate sense oligo was introduced into RAW 264 cells. After changing the medium to a DMEM medium containing 10% bovine fetal serum (1.5 ml per well), the cells were left standing overnight at 37° C. On the next morning, the medium was changed to a DMEM medium containing *Escherichia coli Lipopolysaccharide* (LPS) (1 µg/mg), and the cells were left standing for 4 hours at 37° C. Then, all the obtained RNAs were extracted and subjected to RT-PCR. The obtained all the RNAs were treated with TURBO DNA-free Kit (product of Applied Biosystems.) including DNase to thereby remove genomic DNAs mixed therein.

The sense oligo was prepared for mouse iNOS mRNA corresponding to mouse antisense transcript.

The sequence of mouse iNOS gene sense chain used herein, that is, a phosphorothioate oligonucleotide having the same sequence as iNOS mRNA, can be shown by the following sequences. In the experiments, the sequences correspond to S1, S2 and S3.

```
S1: 5'-G*A*A*GCACTTTGGGTGAC*C*A*C-3'

S2: 5'-T*A*G*CTGCACTATGTACA*G*A*T-3'

S3: 5'-C*A*G*ATATTTATACTTCA*T*A*T-3'
   (Phosphorothioated sites are shown with "*".)
```

The amount of mouse iNOS mRNA was measured according to chain-specific RT-PCR as conducted in Example 4.

As a result, the amount of mouse iNOS RNA was decreased. This shows that a phosphorothioate sense oligo was hybridized to iNOS antisense transcript to thereby decompose or compete against the antisense transcript and also decompose iNOS mRNA (FIG. 3).

[Conclusion Based on Examples 1 to 5]

From the results of Examples 4 and 5, it is shown that not only in case of rat but also in case of mouse, iNOS sense oligo can promote decomposition of iNOS mRNA and then reduce specifically the amount of iNOS mRNA by hybridizing specifically to iNOS antisense transcript.

Thus, expression of iNOS mRNA could be suppressed by using sense oligonucleotide both in rat hepatocyte and in mouse cell. Accordingly, suppression of iNOS mRNA expression by using sense oligonucleotide, which leads to reduction in iNOS induction and NO production at the time of hepatic inflammation, can be said to be an effective method for treating hepatic disorders.

(3) Method for Determining a Sequence and Region (Base Length) of an Antisense Transcript Complementary to mRNA of Early Response Gene Other than iNOS Gene Genes induced to express at the time of inflammation (so-called "early response gene") include not only iNOS but also genes of physiologically active substances such as cytokine and chemokine. These early response genes participate in various actions such as exacerbation or improvement of inflammation. Controlling expression of early response genes eventually leads to controlling inflammation. Given this, other than antisense transcript of iNOS gene, investigation on other early response genes was made as to whether or not antisense transcript was expressed. Next, a presumption was made that antisense transcript of the 3'UTR sequence with high interspecific conservation, containing two or more ARE sequences, was expressed. Then, with respect to this portion, a sense primer for reverse transcription and a pair of primers for PCR were designed. Then, by carrying out chain-specific RT-PCR method on this portion as in Example 4 using rat iNOS gene where antisense transcript was detected, it was checked whether or not antisense transcript was expressed in rat hepatocyte.

Among early response genes other than iNOS gene, three typical types of genes containing two or more ARE sequences in the 3'UTR, with the 3'UTR sequences being analogous to each other between species (human, mouse and rat), were used as examples. Those are the following three genes.
(a) Cytokine-Induced Neutrophil Chemoattractant 1 (CINC-1): This is also called Chemokine (C—X—C motif) Ligand 1 (CXCL1), which is chemokine induced in rat hepatocyte stimulated by IL-1β.
(b) NF-κB p50: This is one of subunits of transcription factor NF-κB, which is a protein deeply involved in inflammation.
(c) IκB-α: This is a protein suppressing activities of NF-κB.

The mRNA base sequences of these genes human, mouse and rat genes are known as published in DDBJ/EMBL/GenBank International Nucleotide Database (http://www.ddbj.nig.ac.jp/, http://www.ebi.ac.uk/embl/, http://www.ncbi.nlm.nih.gov/Genbank/).

Example 6

Rat CINC-1 Antisense Transcript

By the following method, investigation on mRNA of rat CINC-1 was made as to whether or not "antisense transcript" existed. The procedures not described below were carried out in the same manner as in Example 1.

All RNAs were extracted from rat primary-cultured hepatocyte according to a conventional method by using Trizol reagent (product of Invitrogen Corporation) after stimulating the hepatocyte with IL-1β. The obtained all the RNAs were treated with TURBO DNA-free Kit (product of Applied Biosystems.) including DNase to thereby remove genomic DNAs mixed therein. With all the RNAs as templates, reverse transcription was conducted by using the following primer of a sense chain of rat CINC-1 gene: 5'-TGTCTGGTGAACGCTGGCTTCTGA-3'(Sequence No. 16) to thereby synthesize cDNA.

Step-down PCR was carried out in the same manner as in Example 1, by using the obtained cDNA and the following two kinds of primers of sense chain of rat CINC-1 gene:

```
Forward direction:
5'-TGTGGATGCGTTTCATCGATGGT-3'    (Sequence No. 17)

Reverse direction:
5'-CTAGCACAGTGGTTGACACTTA-3'.    (Sequence No. 18)
```

As a result of subjecting the PCR product to agarose gel electrophoresis, amplification of the band of 122 base pairs (bp) was observed. This amplified band was cut out of the gel and purified, and the base sequence was determined. It was confirmed that it was a sequence of 3'UTR of rat CINC-1 mRNA sandwiched between the above primer sequences. That is, presence of antisense transcript of rat CINC-1 gene was evidenced by chain-specific RT-PCR method using a sense primer of iNOS gene. The sequence of rat CINC-1 gene antisense transcript is shown as Sequence No. 19, in terms of cDNA sequence.

Example 7

Rat NF-κB p50 Antisense Transcript

By the following method, investigation on mRNA of rat NF-κB p50 was made as to whether or not "antisense transcript" which had been transcribed from an antisense chain of a gene existed. The procedures not described below were carried out in the same manner as in Example 6.

All RNAs were extracted from rat primary-cultured hepatocyte according to a conventional method by using Trizol reagent (product of Invitrogen Corporation) after stimulating the hepatocyte with IL-1β. The obtained all the RNAs were treated with TURBO DNA-free Kit (product of Applied Biosystems.) including DNase to thereby remove genomic DNAs mixed therein. With all the RNAs as templates, reverse transcription was conducted by using the following primer of a sense chain of rat NF-κB p50 gene: 5'-CTGTCATTAAGGTATCGCAGTCC-3'(Sequence No. 20). to thereby synthesize cDNA.

Step-down PCR was carried out in the same manner as in Example 1, by using the obtained cDNA and the following two kinds of primers of sense chain of rat NF-κB p50 gene:

```
Forward direction:
5'-CATCTACAGTACAGTCATGCACTC-3'    (Sequence No. 21)

Reverse direction:
5'-GGGAAAATACTATTTTCAGCACTGA      (Sequence No. 22)
T-3'.
```

As a result of subjecting the PCR product to agarose gel electrophoresis, amplification of the band of 192 base pairs (bp) was observed. This amplified band was cut out of the gel and purified, and the base sequence was determined. It was confirmed that it was a sequence of 3'UTR of rat NF-κB p50 mRNA sandwiched between the above primer sequences. That is, presence of antisense transcript of rat NF-κB p50 gene was evidenced by chain-specific RT-PCR method using a sense primer of iNOS gene. The sequence of rat NF-κB p50 gene antisense transcript is shown as Sequence No. 23, in terms of cDNA sequence.

Example 8

Rat IκB-α Antisense Transcript

By the following method, investigation on mRNA of rat IκB-α was made as to whether or not "antisense transcript" which had been transcribed from an antisense chain of a gene existed. The procedures not described below were carried out in the same manner as in Example 6.

All RNAs were extracted from rat primary-cultured hepatocyte according to a conventional method by using Trizol reagent (product of Invitrogen Corporation) after stimulating the hepatocyte with IL-1β. The obtained all the RNAs were treated with TURBO DNA-free Kit (product of Applied Biosystems.) including DNase to thereby remove genomic DNAs mixed therein. With all the RNAs as templates, reverse transcription was conducted by using the following primer of a sense chain of rat IκB-α gene: 5'-TCCAGAATCTGATAAAAGGACCAC-3'(Sequence No. 24), to thereby synthesize cDNAs.

Step-down PCR was carried out in the same manner as in Example 1, by using the obtained cDNA and the following two kinds of primers of sense chain of rat IκB-α gene:

```
Forward direction:
5'-TGAACCGCCATAGACTGTAGCTG-3'    (Sequence No. 25)

Reverse direction:
5'-GCACATACCACTGAACACCTGGT-3'.   (Sequence No. 26)
```

As a result of subjecting the PCR product to agarose gel electrophoresis, amplification of the band of 102 base pairs (bp) was observed. This amplified band was cut out of the gel and purified, and the base sequence was determined. It was confirmed that it was a sequence of 3'UTR of rat IκB-α mRNA sandwiched between the above primer sequences. That is, presence of antisense transcript of rat IκB-α gene was evidenced by chain-specific RT-PCR method using a sense primer of iNOS gene. The sequence of rat IκB-α gene antisense transcript is shown as Sequence No. 27, in terms of cDNA sequence.

[Conclusion Based on Examples 6 to 8]

As early response genes other than iNOS gene which are expressed at the time of inflammation, three typical genes (CINC-1NF-κB p50, IκB-α) were selected. All the genes contains two or more ARE sequences in the 3'UTR and the 3'UTR sequences are analogous to each other between the species (human, mouse and rat). As in the case of iNOS, expression of antisense transcripts was confirmed with respect to the three genes.

Based on the above fact, it is assumed that antisense transcripts are molecules common to early response genes containing ARE sequences and 3'UTR sequences analogous to each other between species. Moreover, it is strongly suggested that antisense transcripts probably control stability of the mRNAs. Therefore, it is expected to suppress inflammation by controlling actions of antisense transcripts of early response genes at the time of liver inflammation or the like.

(4) Expression Induction of iNOS and Antisense Transcript In Vivo in Case of Using Rat Model of Acute Hepatic Failure and an Effect of a Liver Protecting Agent (IGF-I & FR183998) for Suppressing Expression Induction of Antisense Transcript The results of Examples 1 and 4 showed that in the system of rat primary-cultured hepatocyte (in vitro), an antisense transcript corresponding to the 3'-untranslated region (3'-UTR) of iNOS mRNA was expressed at the time of inducing iNOS, to promote stabilization of iNOS mRNA. It is also shown below that in rat liver injury model (in vivo), an iNOS antisense transcript (in vivo) was expressed in response to iNOS induction. Further, relationship between changes in survival rate when liver protecting agent such as Insulin-like growth factor-I (IGF-I) and $Na^+/H^+$ exchanger inhibitor (FR183998) is administered and inflammatory cytokines, iNOS mRNA and induction of antisense transcripts is shown below.

Example 9

(I) Preparation of Acute Hepatic Failure Model and Administration of Liver Protecting Agent To male Sprague-Dawley rats (250-300 g), a mixture liquid (D-GalN/LPS) of D-galactosamine (400 g/kg) and LPS (16 μg/kg) which is bacterial endotoxin was intravenously-administered to thereby prepare acute hepatic failure models. Insulin-like growth factor-I (IGF-I; 3.2 mg/kg) or $Na^+/H^+$ exchanger inhibitor (FR183998; 1 mg/kg) was administered 30 minutes before treatment with D-GalN/LPS. Inflammatory cytokines (TNF-α, IL-1β, IL-6, interferon-γ, CINC-1), MIP-2 and nitrogen monoxide in the blood and in the liver were measured. All RNAs were prepared from the liver and iNOS mRNA and iNOS antisense transcript were examined by RT-PCR.

(II) Analysis of RNA 3 or 6 hours after a mixture liquid of D-galactosamine and LPS was intravenously-administered, rat livers were taken out and all RNAs were extracted according to a conventional method by using Trizol reagent (product of Invitrogen Corporation).

With all the RNAs as templates, reverse transcription was conducted by using an oligo dT primer. Then, PCR(RT-PCR method) was carried out in the same manner as in Example 1. In quantitative determination of iNOS mRNA, elongation factor-1α (EF1) mRNA serving as internal standard, oligo dT primer was used in reverse transcription and in PCR, iNOSmRNA:
CCAACCTGCAGGTCTTCGATG (Sequence No. 28) and
GTCGATGCACAACTGGGTGAAC (Sequence No. 29), EFmRNA:
TCTGGTTGGAATGGTGACAACATGC (Sequence No. 30) and
CCAGGAAGAGCTTCACTCAAAGCTT (Sequence No. 31) were used. To the PCR reaction solution, anti-Taq high(=anti-Taq polymerase antibody; product of TOYOBO CO., LTD.) was added.

Quantitative determination of iNOS antisense transcripts was made according to the method of Example 1. By using a control on which PCR was carried out without reverse transcription, it was confirmed that genomes mixed in all RNAs in liver cells were not amplified by PCR. Results of detecting iNOS mRNA were shown in FIG. 4 and results of detecting iNOS antisense transcripts were shown in FIG. 5. In the Figures, RT (−) indicates a negative control of reverse transcription (−).

(III) Quantitative Determination of mRNA and Antisense Transcripts by Real-Time PCR Quantitative determination of the cDNAs synthesized through reverse transcription was made by real-time PCR using iCycler System of Bio-Rad Laboratories, Inc. To the PCR reaction solution, SYBR Green I (product of Roche Diagnostics K.K.) and anti-Taq high (anti-Taq polymerase antibody, manufactured by TOYOBO CO., LTD.) were added, and touchdown PCR, a known method, was carried out. The actually employed PCR protocols were as follows.
1 cycle (94° C., 1 min),
50 cycles (94° C., 30 sec; (72-0.3×n)° C., 1 min; 72° C., 30 sec); n is the number of cycles. The results are shown in FIG. 6. In the Figures, "*" indicates "$p<0.05$ vs. GalN/LPS rat (n=3-6 rat/group)".

(IV) Changes in Amounts of iNOS mRNA and iNOS Antisense Transcripts Due to Liver Protecting Agent In a case where liver protecting agent was not administered, most (more than 90%) of the animals died within about 24 hours after D-GalN/LPS was intravenously-administered. In the blood and the liver, inflammatory mediators (TNF-α, IL-1β, IL-6, interferon-γ, CINC-1, MIP-2, NO) had been increased with time (in 1 to 12 hours). In response to iNOS mRNA induction in the liver, the amount of antisense transcripts showed increase (both the amounts of iNOS mRNAs and antisense transcripts were at their maximum points at 6 hours after the administration and as a result, excessive NO production was observed.

By administration of IGF-I, the death rate was decreased to a range of 20-30% or less. Further, increase in the above-described inflammatory cytokines and production of NO as well as iNOS mRNAs and antisense transcript induction was suppressed (FIGS. 4 to 6).

By administration of FR183998, the death rate was decreased to a range of 20-30% or less. Further, increase in the above-described inflammatory cytokines and production of NO as well as iNOS mRNAs and antisense transcript induction was suppressed (FIGS. 7 to 9).

(IV-1) Effect of Liver Protecting Agent IGF-I on Expression Induction of iNOS mRNAs and Antisense Transcripts in Rat Model of Acute Hepatic Failure In the results of FIG. 4, in rats to which D-galactosamine and LPS were administered (GalN/LPS rats), iNOS mRNA level was increased in 3 to 6 hours while in rats to which IGF-I was administered, such an increase was suppressed.

Based on the results of FIGS. 5 and 6 where almost no cDNAs amplified in RT(−) was observed, it can be assumed that the amount of genomic DNAs got mixed in all the RNAs was extremely small. In GalN/LPS rats, the level of antisense transcripts was increased in 3 to 6 hours while such an increase was suppressed in rats to which IGF-I was administered.

(IV-2) Effect of Liver Protecting Agent FR183998 on Expression Induction of iNOS mRNAs and Antisense Transcripts in Rat Model of Acute Hepatic Failure In the results of FIG. 7, in GalN/LPS rats, iNOS mRNA level was increased in 3 to 6 hours while in rats to which FR183998 was administered, such an increase was suppressed.

Based on the results of FIGS. 8 and 9 where almost no cDNAs amplified in RT(−) was observed, it can be assumed that the amount of genomic DNAs got mixed in all the RNAs was extremely small. In GalN/LPS rats, the level of antisense transcripts was increased in 3 to 6 hours while such an increase was suppressed in rats to which FR183998 was administered.

(5) Effect of Sense Oligo in Rat Hepatocytes (Changes in Amounts of iNOS Proteins and Nitrogen Monoxide (NO))

Example 10

In the same manner as in Example 4, sense oligo S5 or scramble oligo Scr 5 obtained in Example 4 was introduced into hepatocytes and the amount of nitrogen monoxide in the medium was measured by using Nitric Oxide Colorimetric Assay kits (product of Roche Diagnostics K.K.). The measurement was made after the medium was changed to a WE medium containing 1 nm IL-1β on the next morning and left standing at 37° C. for 8 to 10 hours. Also, all the proteins were extracted from the cells and iNOS proteins were detected by Western method using ECL Kit (product of GE Healthcare UK Ltd.). The results are shown in FIG. 10.

As a result, it was shown that by introducing sense oligo S5 into rat hepatocytes, the amounts of iNOS proteins and nitrogen monoxide in the medium were decreased.

(6) Detection of iNOS Antisense Transcripts by Northern Method

Example 11

It was confirmed by Northern blot analysis (hereinafter, simply referred to as "Northern method") that antisense transcripts of iNOS genes were present in rat hepatocytes simulated by IL-1β.

(I) Preparation of RNA

After rat hepatocytes were stimulated by IL-1β for a certain period of time, all RNAs were extracted by using Trizol reagent (manufactured by Invitrogen Corporation). The obtained all the RNAs were treated with TURBO DNA-free Kit (product of Applied Biosystems.) including DNase to thereby remove genomic DNAs mixed therein. Poly(A)+ RNAs and poly(A)− RNAs were fractionated with PolyATract mRNA Isolation System (product of Promega Corporation). In order to prevent nonspecific hybridization, ribosome RNAs (rRNAs) were precipitated in the presence of polyethylene glycol 6000 of final concentration of 5% and NaCl of a final concentration of 0.75 M, to thereby be removed. The supernatant was recovered by ethanol precipitation and used in electrophoresis.

(II) Northern Method/Electrophoresis

The above RNAs, that is, the four types of RNAs, all RNAs of non-stimulated rat hepatocytes, all RNAs of rat hepatocytes stimulated by IL-1β, Poly(A)+ RNAs of rat hepatocytes stimulated by IL-1β and Poly(A)− RNAs of rat hepatocytes stimulated by IL-1β were subjected to electrophoresis with 2.2M formalin-containing agarose and isolated.

(III) Northern Method: Hybridization

According to a conventional method, RNAs in the gel were transferred to Nytran N Filter (product of Whatman PLC.). Next, in DIG EasyHyb buffer (product of Roche Diagnostics K.K.), hybridization to digoxigenin(DIG)-labeled sense probe for iNOS 3'UTR was conducted at 73° C. overnight. On the next morning, according to the manual of Roche Diagnostics K.K., the filter was washed. The sense probe for iNOS 3'UTR used here had been prepared through synthesis of RNAs in a test tube by using DIG-1'-UTP (product of Roche Diagnostics K.K.) and T3 RNA polymerase (product of Stratagene).

(IV) Northern Method: Detection

According to the manual of Roche Diagnostics K.K., blocking was carried out to thereby incubate with anti-DIG antibodies (product of Roche Diagnostics K.K.) conjugated to alkaline phosphatase. After washing, the resultant was reacted with CDP-Star substrate (product of Applied Biosystems.) and bands of RNAs hybridizing to iNOS sense probe were detected through X-ray film.

(V) Results and Consideration

The results of analysis on the 4 kinds of RNAs by Northern method are shown in FIG. 11 (X-ray autoradiogram).

In "all RNAs of rat hepatocyts stimulated by IL-1β" and "Poly(A)-RNAs of rat hepatocyts stimulated by IL-1β", smear-like dark bands of 600 to 1000 nucleotides (nt) were observed. Since sense probe for iNOS 3'UTR was used, these smear-like bands can be considered to be bands of iNOS antisense transcripts. Therefore, it was found out that the lengths of iNOS anti transcripts were not constant, varying from 600 to 1000 nucleotides.

Based on combination of results of RACE and results of ribonuclease protection assay, as shown in FIG. 12, it was assumed that iNOS antisense transcripts had been synthesized. In the Figure, the dotted line indicates that antisense transcripts of various sizes of 600 nucleotides or more were produced. The numbers in the boxes in the Figure refer to exon numbers of iNOS genes, the black parts are protein translated regions, and the white box is 3'UTR at exon 27. The mRNA of iNOS is shown in the upper part of the Figure.

(7) mRNA Stabilization by Excessive Expression of iNOS Antisense Transcripts

Example 12

It was confirmed that mRNAs were stabilized through iNOS 3'UTR by excessive expression of iNOS antisense transcripts in rat hepatocytes.

In a case of a normal reporter, a luciferase gene is connected to an iNOS gene promoter. Since an iNOS gene promoter is "inducible promoter", promoter activity is drastically changed by IL-1β stimulation in rat hepatocytes and it is difficult to observe how the 3' UTR connected behind the reporter gene acts. Therefore, we decided to use a promoter of elongation factor-1α (EF) gene which is a constitutive promoter promoting a constant amount of expression irrespective of stimulation. This, luciferase genes and β-galactosidase genes, controlled by the EF promoter, are expressed in almost constant amounts, irrespective of stimulated or not. By this, observation can be made focusing on influence of iNOS mRNA 3'UTR containing a poly(A) signal sequence on stability of luciferase mRNA.

The following three kinds of vectors were constructed based on pGL3-Basic plasmid (product of Promega Corporation). The outline of the constructed vectors is shown in FIG. 13.

(i) reporter (luciferase vector):
EF promoter+luciferase gene(Luc)+iNOS 3'UTR
EF promoter+luciferase gene(Luc)+SVpA
(Luciferase mRNAs are constitutively-expressed and stability of mRNAs can be controlled by the terminal region of luciferase gene.)

(ii) vector for expressing iNOS antisense transcripts:
CMV promoter+iNOS 3'UTR inserted in the reverse direction+SVpA
(iNOS antisense transcripts are excessively expressed in the cells.)

(iii) internal standard (β-galactosidase vector):
EF promoter+3-galactosidase (lacZ) gene+SVpA
(β-galactosidase mRNAs are constitutively-expressed.)

"SVpA" is a poly(A) signal sequence derived from SV40 virus, known as stable 3'UTR, and an mRNA having SVpA added thereto is not easily destroyed. A CMV promoter which is a control against iNOS 3'UTR, is derived from cytomegalovirus and is a constitutive promoter much stronger than an EF promoter.

When the plasmids of (i) and (iii) are introduced into rat hepatocytes simultaneously, the synthesis amounts of luciferase mRNA (Luc) and β-galactosidase mRNA (βGal) are almost constant, since the EF promoter is constitutive. Moreover, if there is a difference in the amounts between a case where vector for expressing iNOS antisense transcripts (ii) is added and a case where not added, there must be a difference in Luc mRNA/βGal mRNA (Luc/(βGal values). If the Luc/βGal varies depending on the presence of the vector for expressing iNOS antisense transcripts, it leads to a conclusion that excessive expression of iNOS antisense transcripts affected stability of luciferase mRNAs through iNOS 3'UTR.

[Method]
(I) Transfection
Into primary-cultured rat hepatocytes, the following plasmids were introduced according to the above-described method (MATra).
(i) reporter (400 ng/well),
±(ii) vector for expressing iNOS antisense transcripts (50 ng/well)
(iii) internal standard (400 ng/well)

Those having vector for expressing iNOS antisense transcripts introduced therein is referred to as AS(+) and those not having it introduced therein as AS (−).

(II) Preparation of RNA
The medium of hepatocytes was changed after one night after transfection and then all RNAs were extracted time serially. The extraction was conducted by using Trizol reagent (manufactured by Invitrogen Corporation) and all the obtained RNAs were treated according to a conventional method. The obtained all the RNAs were treated with TURBO DNA-free Kit (product of Applied Biosystems.) including DNase to thereby remove genomic DNAs mixed therein. With all the RNAs as templates, reverse transcription was conducted by using an oligo (dT) primer to thereby synthesize cDNAs for mRNAs.

(III) Quantitative Determination of mRNAs by Real-Time PCR

With the thus synthesized cDNAs, quantitative determination was made by real-time PCR. Here, iCycler System of Bio-Rad Laboratories, Inc. was used. To the PCR reaction liquid, SYBR Green I (product of Roche Diagnostics K.K.) and anti-Taq high(=anti-Taq polymerase antibody, manufactured by TOYOBO CO., LTD.) were added and touchdown PCR, a known method, was carried out. The actually employed PCR protocols were as follows.

1 cycle (94° C., 1 min),
50 cycles (94° C., 30 sec; (72-0.3×n)° C., 1 min; 72° C., 30 sec); n is the number of cycles.

The primers used in PCR of reporter luciferase (Luc) mRNA are the following two types.

```
Forward direction:
5'-GCGAAGGTTGTGGATCTGGATAC-3'    (Sequence No. 32)

Reverse direction:
5'-GAGCCACCTGATAGCCTTTGTAC-3'    (Sequence No. 33)
```

The primers used in PCR of internal standard β-galactosidase (βGal) mRNA are the following two types.

```
Forward direction:
5'-GTCACACTACGTCTGAACGTCGA-3'    (Sequence No. 34)

Reverse direction:
5'-TGCAGAGGATGATGCTCGTGACG-3'    (Sequence No. 35)
```

After real-time PCR was carried out, threshold cycle (Ct) values of luciferase mRNA (Luc) and β-galactosidase mRNA (βGal) were calculated by using iCycler system analysis software and the values were divided to obtain a Luc/βGal value.

[Results]
Time-serial Luc/(3-Gal values in cases including or not including addition of vector for expressing iNOS antisense transcripts were calculated and the results are shown in FIG. 14.

(i) reporter (EF promoter+Luc+iNOS 3'UTR)
±(ii) vector for expressing iNOS antisense transcripts
(iii) internal standard In the cases, when AS (+) of cases including addition of vector for expressing iNOS antisense transcripts is compared with AS(−) of cases not including addition of vector for expressing iNOS antisense transcripts, the Luc/β-Gal value was significantly increased. In the Figure, "**" indicates "p<0.01 versus AS(−)". That is, iNOS antisense transcripts stabilized luciferase mRNAs via iNOS 3'UTR.

As a control, the results of a case using an SVpA-connected reporter are shown in FIG. 15.

(i) reporter (EF promoter+Luc+SVpA)
±(ii) vector for expressing iNOS antisense transcripts
(iii) internal standard.

In the cases, when AS (+) (cases including addition of vector for expressing iNOS antisense transcripts) is compared with AS(−) (cases not including addition of vector for expressing iNOS antisense transcripts), the Luc/βGal value was not increased. That is, SVpA had no influence on stabilization of mRNAs.

[Significance]

Based on the above results (experiments on excessive expression of iNOS antisense transcripts), it can be assumed that iNOS antisense transcripts act on iNOS 3'UTR to thereby stabilize mRNAs. Based on the above combined with the results of iNOS mRNA knockdown experiments using phosphorothioate sense oligonucleotide, iNOS antisense transcripts can be said to stabilize iNOS mRNAs via iNOS 3'UTR.

Accordingly, it is strongly suggested that the mechanism of iNOS mRNA stability control by iNOS antisense transcripts plays a significant role at the time of liver inflammation or the like. Also, the mechanism can be a target treatment for many diseases related to NO.

[Industrial Applicability]

By administration of liver protecting agent, induction of iNOS mRNA and antisense transcripts was suppressed. The above results strongly suggest that antisense transcripts are involved (in vivo) as a factor controlling expression induction of iNOS mRNAs. It is assumed that the antisense transcript expression control by use of liver protecting agent reduces iNOS induction and NO production at the time of liver inflammation or the like and can be an effective treatment method for hepatic disorders.

SEQUENCE LISTING

Figure 1:
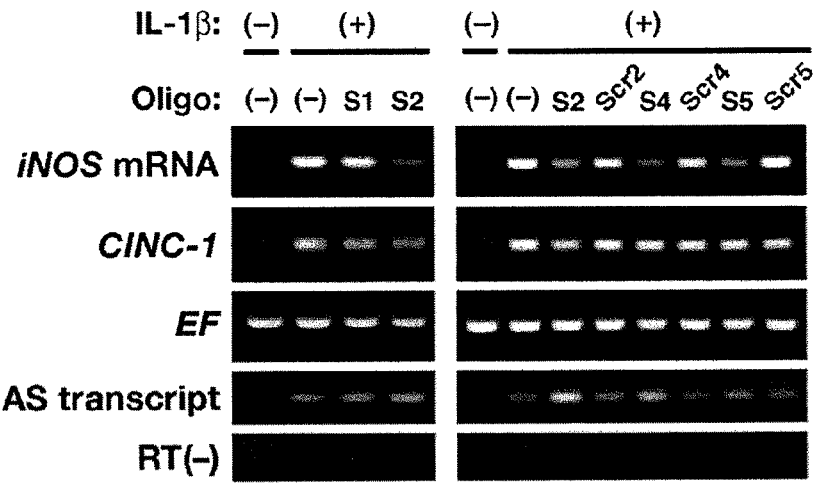
FIG. 1 is an electrophoretogram showing measurement results of mRNA amounts in rat hepatocytes by RT-PCR method.
Figure 2:
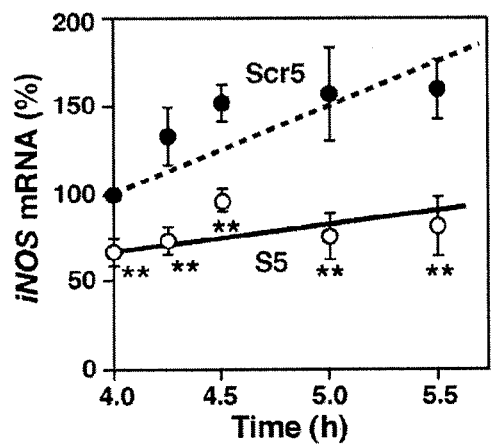
FIG. 2 is a graph showing measurement results of mRNA amounts in rat hepatocytes by real-time PCR method.
Figure 3:
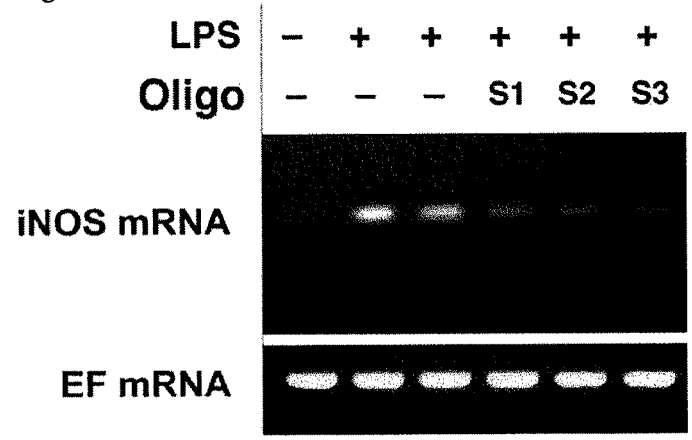
FIG. 3 is an electrophoretogram showing that iNOS mRNAs were decomposed by mouse iNOS antisense transcripts.
Figure 4:
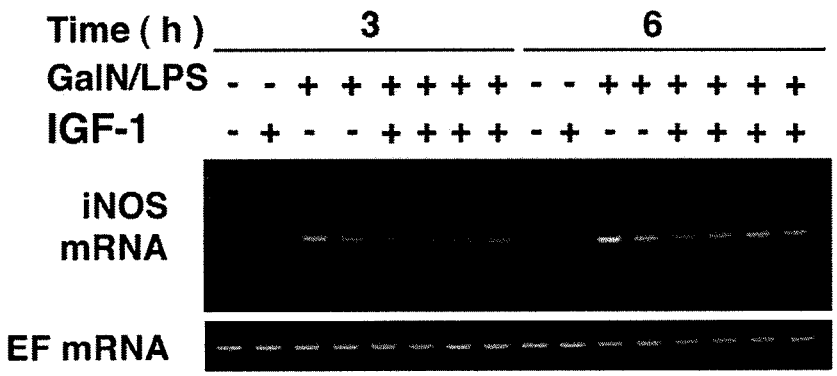
FIG. 4 is an electrophoretogram showing results of detecting iNOS mRNAs by chain-specific RT-PCR method, which shows that increase of iNOS mRNAs in rats to which liver protecting agent (IGF-I) was administered was suppressed.
Figure 5:
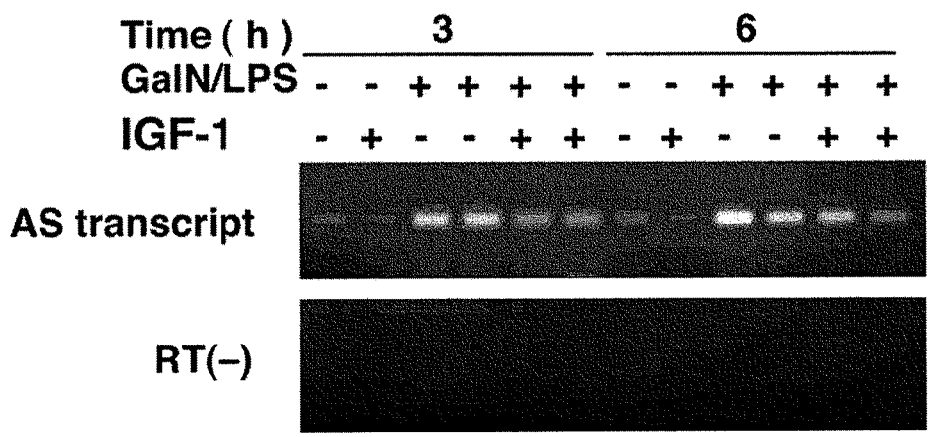
FIG. 5 shows results of detecting iNOS antisense transcripts (an electrophoretogram) by chain-specific RT-PCR method, which shows that increase of iNOS antisense transcripts in rats to which liver protecting agent (IGF-I) was administered was suppressed.
Figure 6:
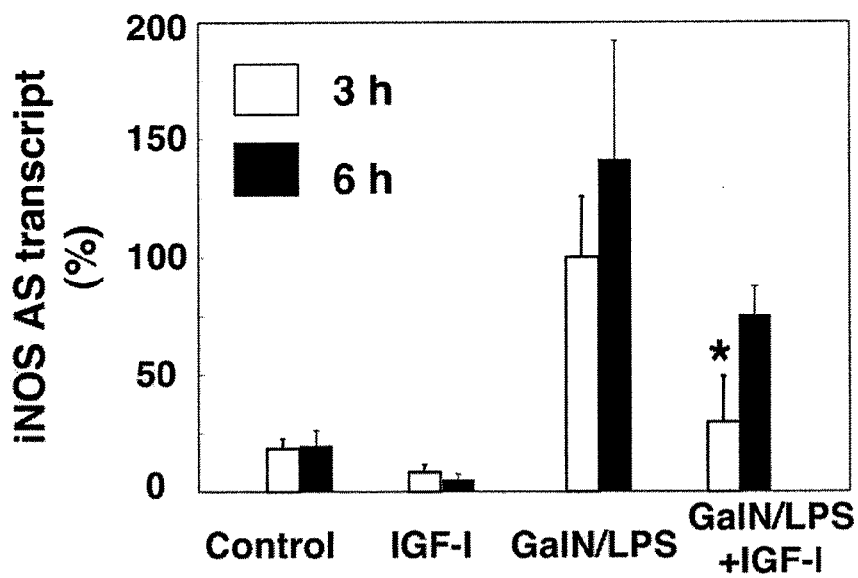
FIG. 6 is a graph showing results of quantitative determination of increase of iNOS antisense transcripts by real-time PCR method in rats to which liver protecting agent (IGF-I) was administered. In the Figure, "*" indicates "p<0.05 vs. GalN/LPSrat (n=3-6 rats/group).
Figure 7:
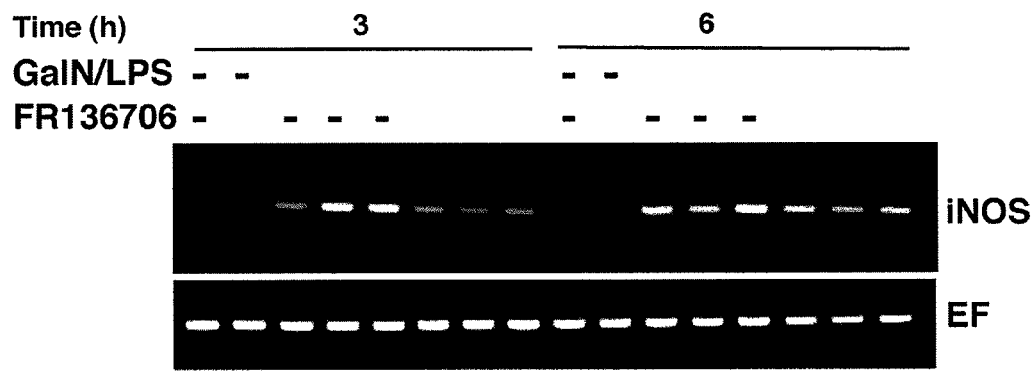
FIG. 7 is an electrophoretogram showing results of detecting iNOS mRNAs by chain-specific RT-PCR method, which shows that increase of iNOS mRNAs in rats to which liver protecting agent (FR183998) was administered was suppressed.
Figure 8:
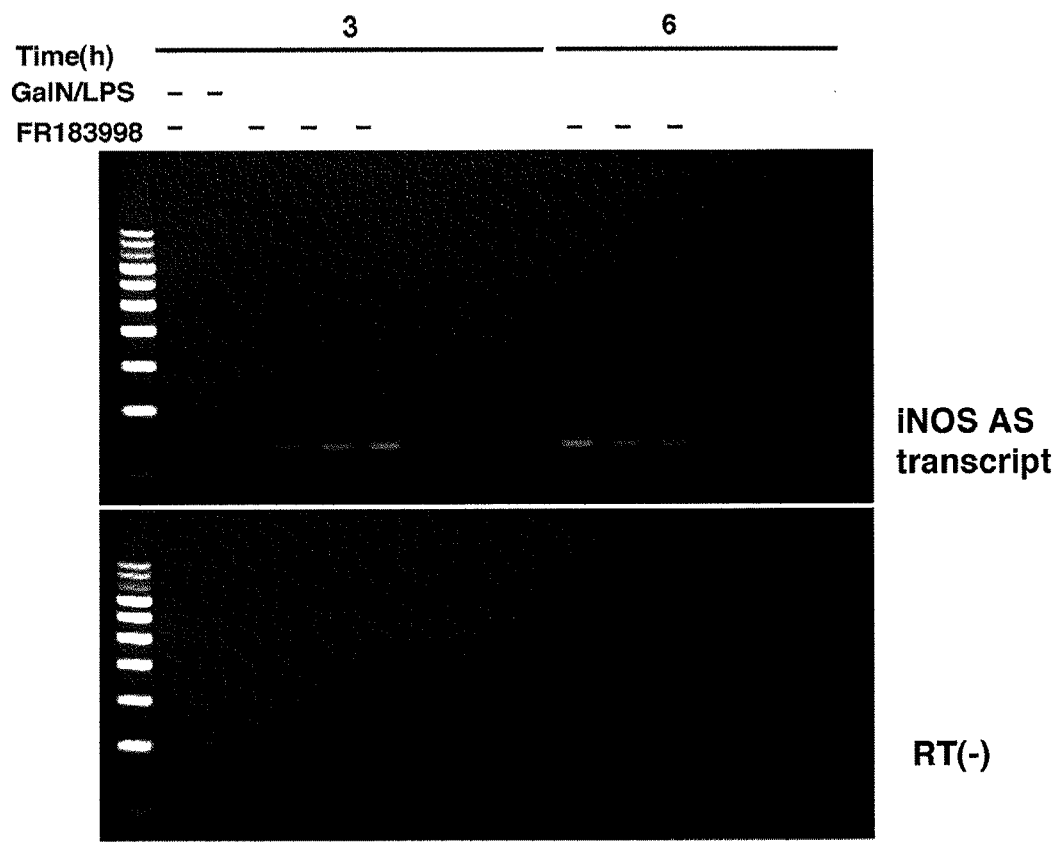
FIG. 8 shows results of detecting iNOS antisense transcripts (an electrophoretogram) by chain-specific RT-PCR method, which shows that increase of iNOS antisense transcripts in rats to which liver protecting agent ((FR183998) was administered was suppressed.
Figure 9:
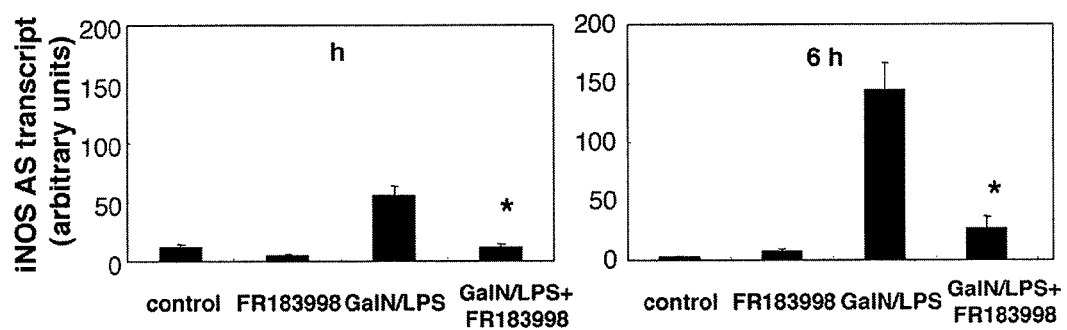
FIG. 9 is a graph showing results of quantitative determination of increase of iNOS antisense transcripts by real-time PCR method in rats to which liver protecting agent (FR183998) was administered. In the Figure, "*" indicates "p<0.05 vs. GalN/LPS rat (n=3-6 rats/group).
Figure 10:
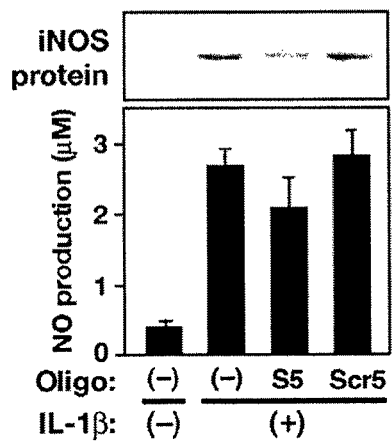
FIG. 10 shows an electrophoretogram and a graph showing results of measuring the amounts of iNOS proteins and nitrogen monoxide in the medium in Example 10.
Figure 11:
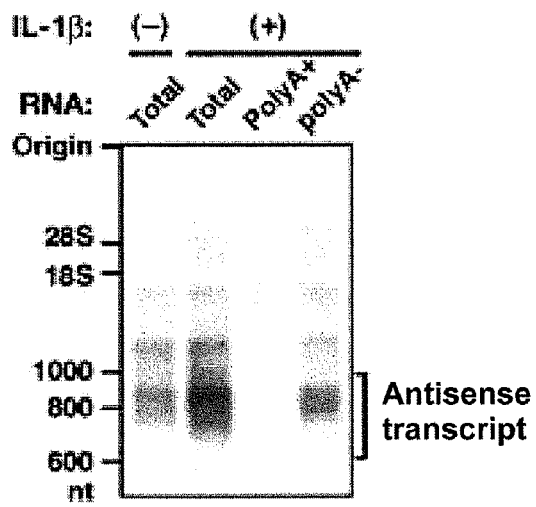
FIG. 11 is an X-ray film autoradiogram showing the analysis results on the four types of RNAs by Northern method in Example 11. From the left, there are shown the results of "all RNAs of non-stimulated rat hepatocytes", "all RNAs of rat hepatocyts stimulated by IL-1β", "Poly(A)$^+$ RNAs of rat hepatocyts stimulated by IL-1β", "Poly(A)$^-$ RNAs of rat hepatocyts stimulated by IL-1β".
Figure 12:
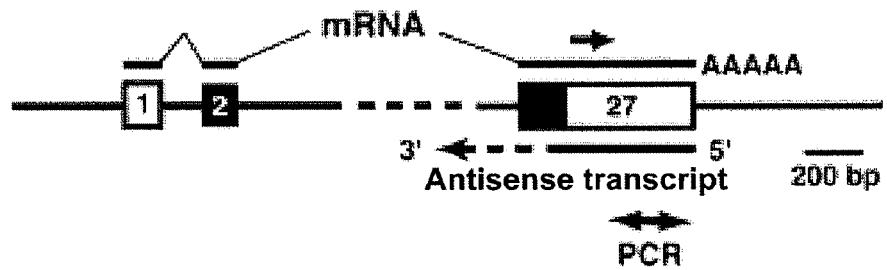
FIG. 12 shows the results of RACE and ribonuclease protection assay in Example 11.
Figure 13:
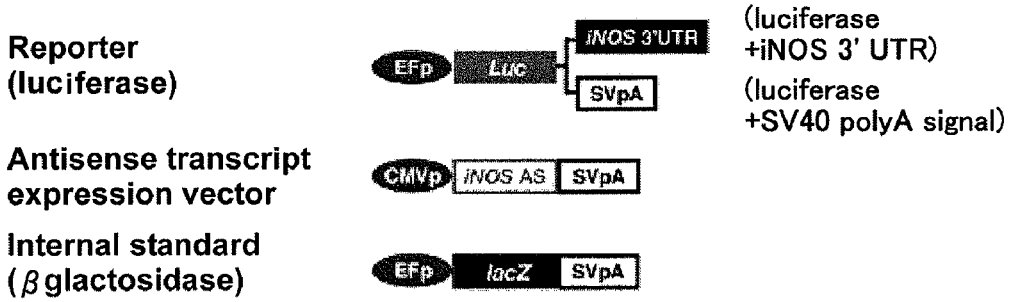
FIG. 13 shows the outline of vectors constructed in Example 12.
Figure 14:
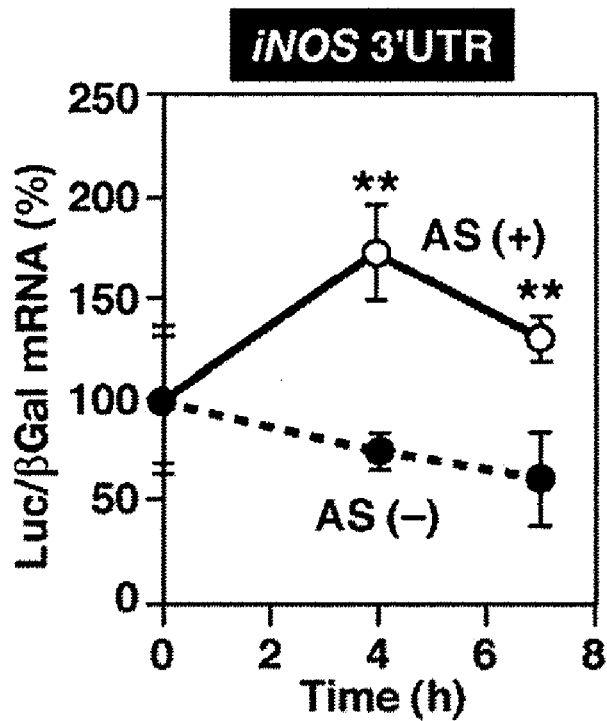
FIG. 14 is a graph showing Luc/βGal values changing with time in cases where the vector for expressing iNOS antisense transcripts was added (AS(+)) and cases without adding the vector (AS(−)) in Example 12.
Figure 15:
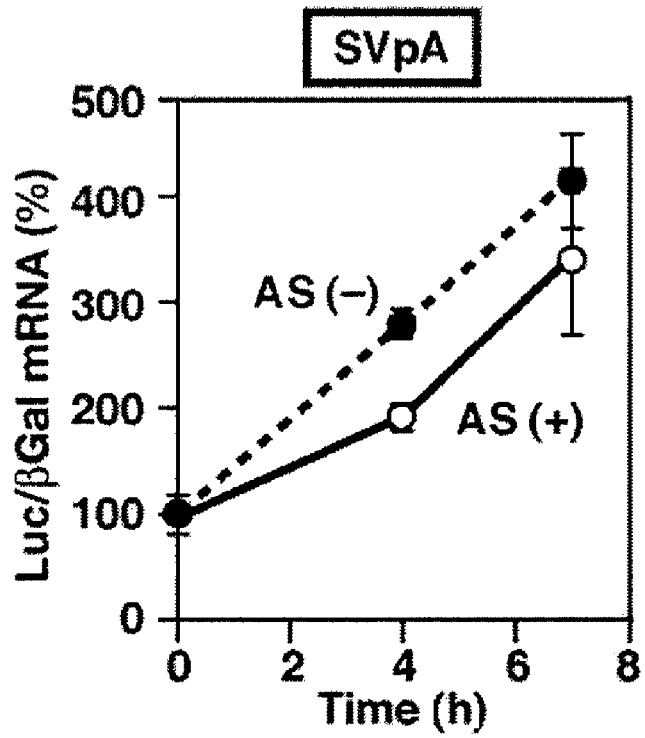
FIG. 15 is a graph showing Luc/βGal values changing with time in a case as control where SVpA-connected reporter was used in Example 12.

```
<160> NUMBER OF SEQ ID NOS: 38

<210> SEQ ID NO 1
<211> LENGTH: 572
<212> TYPE: DNA
<213> ORGANISM: Artificial Sequence
<220> FEATURE:
<223> OTHER INFORMATION: antisense

<400> SEQUENCE: 1
atcaaacact catttttatta aaataaaatg cattttatat aaatatcttc atcaaggaat      60
tatacacgga agggccaagc ggtcgttggg agtggacgaa ggtatgtttt cttaaataca     120
aagtataaat atctgtacac aatgcagcta aatattagag cagcgggatg gcgcctcctg     180
gtggtcaccc aaagtgcttc agtcgggtgg ttcattttcc tctgctctca gctctgagga     240
agtatgaggc aaaggaaaga gaatgtgggg gaggggcaga gaaacggga gggaagggag     300
```

```
aataggggac gggggagagg agagagattc agtagtccac aatagtacaa tactacttgg    360
tagggtagag gaggggagat gatgtgaggg gtttgggggg gatcgcactt ctgtctctcc    420 aaaccccctca ctgtcatttt atttagggcc agatgctgta actcttctgg gtgtcagagt  480
cttgtgcctt tgggctcctc caaggtgttg ccctttttg ctccatagga aaagaccgca    540
ccgaagatat cctcatgata acgtttctgg ct                                  572

<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2
tgcccctccc ccacattctc t                                              21

<210> SEQ ID NO 3
<211> LENGTH: 23
<212> TYPE: DNA
<213> ORGANISM: Artificial Sequence
<220> FEATURE:
<223> OTHER INFORMATION: forward primer

<400> SEQUENCE: 3
accaggaggc gccatcccgc tgc                                            23

<210> SEQ ID NO 4
<211> LENGTH: 26
<212> TYPE: DNA
<213> ORGANISM: Artificial Sequence
<220> FEATURE:
<223> OTHER INFORMATION: reverse primer

<400> SEQUENCE: 4
cttgatcaaa cactcatttt attaaa                                         26

<210> SEQ ID NO 5
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (44)..(50)
<223> OTHER INFORMATION: n=a, c, g or t

<400> SEQUENCE: 5
ttccctcccg ttttctctgc cactagaatt ctcgagcggc cgcnnnnnnn               50

<210> SEQ ID NO 6
<211> LENGTH: 26
<212> TYPE: DNA
<213> ORGANISM: Artificial Sequence
<220> FEATURE:
<223> OTHER INFORMATION: primer

<400> SEQUENCE: 6
atattagagc agcgggatgg cgcctc                                         26

<210> SEQ ID NO 7
<211> LENGTH: 22
<212> TYPE: DNA
<213> ORGANISM: Artificial Sequence
<220> FEATURE:
```

-continued

<223> OTHER INFORMATION: primer

<400> SEQUENCE: 7
actagaattc tcgagcggcc gc                                              22

<210> SEQ ID NO 8
<211> LENGTH: 23
<212> TYPE: DNA
<213> ORGANISM: Artificial Sequence
<220> FEATURE:
<223> OTHER INFORMATION: primer

<400> SEQUENCE: 8
ctgagtgcac cacttcaagt gac                                             23

<210> SEQ ID NO 9
<211> LENGTH: 22
<212> TYPE: DNA
<213> ORGANISM: Artificial Sequence
<220> FEATURE:
<223> OTHER INFORMATION: forward primer

<400> SEQUENCE: 9
caggaggtgc tatcgcacca ct                                              22

<210> SEQ ID NO 10
<211> LENGTH: 24
<212> TYPE: DNA
<213> ORGANISM: Artificial Sequence
<220> FEATURE:
<223> OTHER INFORMATION: reverse primer

<400> SEQUENCE: 10
gcaattcatg taaatatctc catc                                            24

<210> SEQ ID NO 11
<211> LENGTH: 177
<212> TYPE: DNA
<213> ORGANISM: Artificial Sequence
<220> FEATURE:
<223> OTHER INFORMATION: antisense

<400> SEQUENCE: 11
gcaattcatg taaatatctc catcaaggaa tcatacaggg aagacccaag tggccatggg     60
gaacagactg ggtgttagtt ttttaaatac agaggcataa ataactgtac acaaggcagt    120
taaatacaca gtggtgcgat agcacctcct ggtggtcact tgaagtggtg cactcag       177

<210> SEQ ID NO 12
<211> LENGTH: 22
<212> TYPE: DNA
<213> ORGANISM: Artificial Sequence
<220> FEATURE:
<223> OTHER INFORMATION: primer

<400> SEQUENCE: 12
ccttcttctc cactccccag ct                                              22

<210> SEQ ID NO 13
<211> LENGTH: 23
<212> TYPE: DNA
<213> ORGANISM: Artificial Sequence
<220> FEATURE:
<223> OTHER INFORMATION: forward primer

<400> SEQUENCE: 13

```
gaccaccagg aggcaccatg ccg                                              23

<210> SEQ ID NO 14
<211> LENGTH: 23
<212> TYPE: DNA
<213> ORGANISM: Artificial Sequence
<220> FEATURE:
<223> OTHER INFORMATION: reverse primer

<400> SEQUENCE: 14
atacaggaaa ggcccaagcc atc                                              23

<210> SEQ ID NO 15
<211> LENGTH: 240
<212> TYPE: DNA
<213> ORGANISM: Artificial Sequence
<220> FEATURE:
<223> OTHER INFORMATION: antisense

<400> SEQUENCE: 15
atacaggaaa ggcccaagcc atcattggga gtagacaaaa gtatctgttt tcttaaatat      60
gaagtataaa tatctgtaca tagtgcagct aagtattaga gcggcggcat ggtgcctcct     120
ggtggtcacc caaagtgctt cagtcaggag gttgagtttt tctctgctct cagctccaag    180
gaagagtgag aggcaaagga ggagaaggag aaggagggag ctggggagtg gagaagaagg    240

<210> SEQ ID NO 16
<211> LENGTH: 24
<212> TYPE: DNA
<213> ORGANISM: Artificial Sequence
<220> FEATURE:
<223> OTHER INFORMATION: primer

<400> SEQUENCE: 16
tgtctggtga acgctggctt ctga                                             24

<210> SEQ ID NO 17
<211> LENGTH: 23
<212> TYPE: DNA
<213> ORGANISM: Artificial Sequence
<220> FEATURE:
<223> OTHER INFORMATION: forward primer

<400> SEQUENCE: 17
tgtggatgcg tttcatcgat ggt                                              23

<210> SEQ ID NO 18
<211> LENGTH: 22
<212> TYPE: DNA
<213> ORGANISM: Artificial Sequence
<220> FEATURE:
<223> OTHER INFORMATION: reverse primer

<400> SEQUENCE: 18
ctagcacagt ggttgacact ta                                               22

<210> SEQ ID NO 19
<211> LENGTH: 255
<212> TYPE: DNA
<213> ORGANISM: Artificial Sequence
<220> FEATURE:
<223> OTHER INFORMATION: antisense

<400> SEQUENCE: 19
ctagcacagt ggttgacact taatggtctc ccaataaata ttaatttaac gagatattta      60
```

```
acgcctacca tctttaaact gcacaattgg aattgaacga ccatcgatga aacgcatcca      120
catcgttaaa tattaatgta aaataaaaac cacacacttg gtggaataaa taaatacata      180
aaataaatag gaccctcaat agaaatcgta aaatgtgtaa aactagtgtt gtcagaagcc      240
agcgttcacc agaca                                                       255

<210> SEQ ID NO 20
<211> LENGTH: 23
<212> TYPE: DNA
<213> ORGANISM: Artificial Sequence
<220> FEATURE:
<223> OTHER INFORMATION: primer

<400> SEQUENCE: 20
ctgtcattaa ggtatcgcag tcc                                              23

<210> SEQ ID NO 21
<211> LENGTH: 24
<212> TYPE: DNA
<213> ORGANISM: Artificial Sequence
<220> FEATURE:
<223> OTHER INFORMATION: forward primer

<400> SEQUENCE: 21
catctacagt acagtcatgc actc                                             24

<210> SEQ ID NO 22
<211> LENGTH: 26
<212> TYPE: DNA
<213> ORGANISM: Artificial Sequence
<220> FEATURE:
<223> OTHER INFORMATION: reverse primer

<400> SEQUENCE: 22
gggaaaatac tattttcagc actgat                                           26

<210> SEQ ID NO 23
<211> LENGTH: 236
<212> TYPE: DNA
<213> ORGANISM: Artificial Sequence
<220> FEATURE:
<223> OTHER INFORMATION: antisense

<400> SEQUENCE: 23
gggaaaatac tattttcagc actgattata gcaggtttta atattgttaa agttcatgtc      60 ttttttttt ttaaatcaca gataaaccac attagaaaaa gccatgtctt tttttttattg     120 cgcatgaagt tactcactta aaaatatctt tttccttaat cttaatttga gtgcatgact    180
gtactgtaga tggctagaaa gaacaccagg tggggactgc gataccttaa tgacag        236

<210> SEQ ID NO 24
<211> LENGTH: 24
<212> TYPE: DNA
<213> ORGANISM: Artificial Sequence
<220> FEATURE:
<223> OTHER INFORMATION: primer

<400> SEQUENCE: 24
tccagaatct gataaaagga ccac                                             24

<210> SEQ ID NO 25
<211> LENGTH: 23
<212> TYPE: DNA
<213> ORGANISM: Artificial Sequence
<220> FEATURE:
```

<223> OTHER INFORMATION: forward primer

<400> SEQUENCE: 25
tgaaccgcca tagactgtag ctg                                    23

<210> SEQ ID NO 26
<211> LENGTH: 23
<212> TYPE: DNA
<213> ORGANISM: Artificial Sequence
<220> FEATURE:
<223> OTHER INFORMATION: reverse primer

<400> SEQUENCE: 26
gcacatacca ctgaacacct ggt                                    23

<210> SEQ ID NO 27
<211> LENGTH: 119
<212> TYPE: DNA
<213> ORGANISM: Artificial Sequence
<220> FEATURE:
<223> OTHER INFORMATION: antisense

<400> SEQUENCE: 27
gcacatacca ctgaacacct ggttcttacg tgagagggca cactggggtc agctacagtc    60
tatggcggtt caaccaaaag cacaataaat aaaatgtggt cctttatca gattctgga    119

<210> SEQ ID NO 28
<211> LENGTH: 21
<212> TYPE: DNA
<213> ORGANISM: Artificial Sequence
<220> FEATURE:
<223> OTHER INFORMATION: primer

<400> SEQUENCE: 28
ccaacctgca ggtcttcgat g                                      21

<210> SEQ ID NO 29
<211> LENGTH: 22
<212> TYPE: DNA
<213> ORGANISM: Artificial Sequence
<220> FEATURE:
<223> OTHER INFORMATION: primer

<400> SEQUENCE: 29
gtcgatgcac aactgggtga ac                                     22

<210> SEQ ID NO 30
<211> LENGTH: 25
<212> TYPE: DNA
<213> ORGANISM: Artificial Sequence
<220> FEATURE:
<223> OTHER INFORMATION: primer

<400> SEQUENCE: 30
tctggttgga atggtgacaa catgc                                  25

<210> SEQ ID NO 31
<211> LENGTH: 25
<212> TYPE: DNA
<213> ORGANISM: Artificial Sequence
<220> FEATURE:
<223> OTHER INFORMATION: primer

<400> SEQUENCE: 31
ccaggaagag cttcactcaa agctt                                  25

```
<210> SEQ ID NO 32
<211> LENGTH: 23
<212> TYPE: DNA
<213> ORGANISM: Artificial Sequence
<220> FEATURE:
<223> OTHER INFORMATION: forward primer

<400> SEQUENCE: 32
gcgaaggttg tggatctgga tac                                              23

<210> SEQ ID NO 33
<211> LENGTH: 23
<212> TYPE: DNA
<213> ORGANISM: Artificial Sequence
<220> FEATURE:
<223> OTHER INFORMATION: reverse primer

<400> SEQUENCE: 33
gagccacctg atagcctttg tac                                              23

<210> SEQ ID NO 34
<211> LENGTH: 23
<212> TYPE: DNA
<213> ORGANISM: Artificial Sequence
<220> FEATURE:
<223> OTHER INFORMATION: forward primer

<400> SEQUENCE: 34
gtcacactac gtctgaacgt cga                                              23

<210> SEQ ID NO 35
<211> LENGTH: 23
<212> TYPE: DNA
<213> ORGANISM: Artificial Sequence
<220> FEATURE:
<223> OTHER INFORMATION: reverse primer

<400> SEQUENCE: 35
tgcagaggat gatgctcgtg acg                                              23

<210> SEQ ID NO 36
<211> LENGTH: 20
<212> TYPE: DNA
<213> ORGANISM: Artificial Sequence
<220> FEATURE:
<223> OTHER INFORMATION: senseoligo-S2

<400> SEQUENCE: 36
gcctcatact tcctcagagc                                                  20

<210> SEQ ID NO 37
<211> LENGTH: 20
<212> TYPE: DNA
<213> ORGANISM: Artificial Sequence
<220> FEATURE:
<223> OTHER INFORMATION: senseoligo-S4

<400> SEQUENCE: 37
tagctgcatt gtgtacagat                                                  20

<210> SEQ ID NO 38
<211> LENGTH: 20
<212> TYPE: DNA
<213> ORGANISM: Artificial Sequence
<220> FEATURE:
<223> OTHER INFORMATION: senseoligo-S5
```

```
<400> SEQUENCE: 38
gtgtataatt ccttgatgaa                                              20
```

The invention calimed is:

1. A method for increasing the amount of an intracellular early-response protein selected from the group consisting of inducible Nitric Oxide Synthase (iNOS), Cytokine-Induced Neutrophil Chemoattractant-1 (CINC-1) and IκB, comprising introducing into a cell an antisense RNA comprising a nucleotide sequence complementary to the 3'-untranslated region (UTR) of an mRNA encoding iNOS, CINC-1 or IκB;

whereby the introduction of said antisense RNA comprising a nucleotide sequence complementary to the 3'-untranslated region (UTR) of an mRNA encoding iNOS, CINC-1 or IκB into said cell increases the amount of intracellular iNOS, CINC-1 or IκB, respectively.

2. The method of claim 1, wherein said intracellular early-response protein is iNOS.

3. The method of claim 2, wherein said iNOS is human iNOS.

* * * * *